(12) United States Patent
van Dam et al.

(10) Patent No.: US 11,612,349 B2
(45) Date of Patent: *Mar. 28, 2023

(54) HEART CONDITION DETERMINATION METHOD AND SYSTEM

(71) Applicant: Peacs Investments B.V., Nieuwerbrug aan den Rijn (NL)

(72) Inventors: Eelco Matthias van Dam, Arnhem (NL); Peter Michael van Dam, Arnhem (NL)

(73) Assignee: Peacs Investments B.V., Nieuwerbrug aan den Rijn (NL)

( * ) Notice: Subject to any disclaimer, the term of this patent is extended or adjusted under 35 U.S.C. 154(b) by 410 days.

This patent is subject to a terminal disclaimer.

(21) Appl. No.: 16/605,286

(22) PCT Filed: Apr. 12, 2018

(86) PCT No.: PCT/NL2018/050228
§ 371 (c)(1),
(2) Date: Oct. 15, 2019

(87) PCT Pub. No.: WO2018/190715
PCT Pub. Date: Oct. 18, 2018

(65) Prior Publication Data
US 2020/0046243 A1     Feb. 13, 2020

(30) Foreign Application Priority Data

Apr. 12, 2017  (WO) ............... PCT/NL2017/050225

(51) Int. Cl.
*A61B 5/341* (2021.01)
*G16H 50/50* (2018.01)
(Continued)

(52) U.S. Cl.
CPC ............ *A61B 5/341* (2021.01); *A61B 5/282* (2021.01); *A61B 5/318* (2021.01); *A61B 5/339* (2021.01);
(Continued)

(58) Field of Classification Search
None
See application file for complete search history.

(56) References Cited

U.S. PATENT DOCUMENTS

| 2010/0168594 A1 | 7/2010 | Chuang |
| 2012/0143277 A1 | 6/2012 | Ding et al. |

(Continued)

FOREIGN PATENT DOCUMENTS

WO     2017099582 A2     6/2017

OTHER PUBLICATIONS

Jiang et al. (Optimization of the Electrode Positions of Multichannel ECG for the Reconstruction of Ischemic Areas by Solving the Inverse Electrocardiographic Problem, International Journal of Bioelectromagnetism, vol. 11, 2009) (Year: 2009).*

(Continued)

*Primary Examiner* — Kyle Zhai
(74) *Attorney, Agent, or Firm* — The Webb Law Firm

(57) ABSTRACT

The present invention relates to a method to provide a mean temporal spatial isochrone (TSI) path relating to an ECG feature (wave form) of interest, such as the activation of the heart from a single point (QRS), relative to the heart in a torso while using an ECG measurement from an ECG recording device. The method includes: receiving ECG measuring data from the ECG recording device; determining vector cardiogram (VCG) data; receiving a model of the heart, preferably with torso, as an input, preferably based on a request including request parameters; determining mean TSI data values representing the TSI path relating to an (Continued)

electrophysiological phase representing the ECG feature, the mean TSI providing a location within the heart representing the mean location of the ECG feature at the corresponding time; positioning the mean TSI path and preferably the vector cardiogram data points in the model of the heart and/or torso at an initial position; and rendering the model of the heart, preferably with torso, with the mean TSI path, preferably with VCG data related to the TSI, for displaying on a display screen for interpretation of the displayed rendering.

19 Claims, 12 Drawing Sheets

(51) Int. Cl.
| | |
|---|---|
| *G06F 17/18* | (2006.01) |
| *G06T 15/00* | (2011.01) |
| *G16H 40/63* | (2018.01) |
| *G06T 19/20* | (2011.01) |
| *A61B 5/282* | (2021.01) |
| *A61B 5/318* | (2021.01) |
| *A61B 5/339* | (2021.01) |
| *A61B 5/366* | (2021.01) |

(52) U.S. Cl.
CPC .............. *A61B 5/366* (2021.01); *G06F 17/18* (2013.01); *G06T 15/00* (2013.01); *G06T 19/20* (2013.01); *G16H 40/63* (2018.01); *G16H 50/50* (2018.01); *G06T 2210/41* (2013.01); *G06T 2219/2004* (2013.01)

(56) References Cited

U.S. PATENT DOCUMENTS

| | | | |
|---|---|---|---|
| 2012/0157822 A1 | 6/2012 | van Dam et al. | |
| 2015/0320331 A1* | 11/2015 | Van Dam | ............... A61B 5/316 600/509 |
| 2017/0071492 A1 | 3/2017 | van Dam et al. | |
| 2019/0060006 A1 | 2/2019 | van Dam et al. | |

OTHER PUBLICATIONS

Yang et al., "Spatiotemporal representation of cardiac vectorcardiogram (VCG) signals", Biomedical Engineering Online, 2012, pp. 1-15, vol. 11, No. 1.

* cited by examiner

HEART CONDITION DETERMINATION METHOD AND SYSTEM

CROSS-REFERENCE TO RELATED APPLICATIONS

This application is the United States national phase of International Application No. PCT/NL2018/050228 filed Apr. 12, 2018, and claims priority to International Application No. PCT/NL2017/050225 filed Apr. 12, 2017, the disclosures of which are hereby incorporated by reference in their entirety.

BACKGROUND OF THE INVENTION

Field of the Invention

The present invention relates to a method to provide a mean temporal spatial isochrone (TSI) path relating to an ECG feature (wave form) of interest, such as the activation of the heart from a single point (QRS), relative to the heart in a torso while using an ECG measurement from an ECG recording device. Furthermore, the present invention relates to a system performing a method to that effect.

Description of Related Art

A vector cardiogram (VCG) signal is a signal with x,y,z coordinates per time sample. Such a VCG represents the direction of activation in the heart and can be viewed as a single dipole model. This model is thus a simplification of the complex electrical activity (activation and recovery) of the myocardial tissue. There are several existing methods to obtain a VCG signal from ECG signals, such as a frontal mean QRS axis from only the aVr, aVl, aVf, and lead I, II, and III, a Gabor Nelson system, a Frank lead system, or a statistical based transformation matrix, e.g. Dower or Kors transform.

To a doctor, such a vector cardiogram can provide an idea of the development of an activation of the myocardium. However, it requires a lot of experience to use it on the real body as there is only a representation in the form of the ECG loop relative to a starting point at which or from which it is graphically represented, the starting point not providing a relation to the physics of a patient.

SUMMARY OF THE INVENTION

In order to improve upon the prior art, the present invention provides a method to provide a mean temporal spatial isochrone (TSI) path relating to an ECG feature (wave form) of interest, such as the activation of the heart from a single point (QRS), relative to the heart in a torso while using an ECG measurement from an ECG recording device, the method comprising steps of:

receiving ECG measuring data from the ECG recording device, determining vector cardiogram (VCG) data, receiving a model of the heart, preferably with torso, as an input, preferably based on a request comprising request parameters, obtaining the location information relating to a number of ECG electrodes relative to the torso model and or hearts model of the subject, based on the location information in the torso model and/or heart model, positioning of the number of ECG electrodes, determining mean TSI data values representing the TSI path relating to an electrophysiological phase representing the ECG feature, the mean TSI providing a location within the heart representing the mean location of the ECG feature at the corresponding time, positioning the mean TSI path and preferably the vector cardiogram data points in the model of the heart and/or torso at an initial position, rendering the model of the heart, preferably with torso, with the mean TSI path, preferably with VCG data related to the TSI, for displaying on a display screen for interpretation of the displayed rendering.

An advantage of applying a method according to the present invention is that it is directly related to the actual physical location of the heart as the mean TSI path is related to the vector cardiogram data, which is related to the model of the heart by means of the known locations of the electrodes of the ECG recorder.

According to a first preferred embodiment, the steps of positioning the mean TSI path comprise steps for using a predetermined position, such as the center of mass of a heart, for positioning the first data value of the TSI path. By performing the steps, and initial match between the mean TSI path and the heart as it is in the body is created. The better this initial position is chosen, the better the actual mean TSI path fits with the reality within the heart.

According to a further preferred embodiment, the steps of positioning the mean TSI path comprise steps of determining at least one initial position in which the first data point of mean TSI path is to be positioned, preferably such that this position is located in the myocardium.

Both the beginning and the end of the mean TSI path are preferably located within the myocardium. As such, the steps of finding positions in which the $1^{st}$ data point of the mean TSI path is located in the myocardium provide a basis for further processing of the method.

Further preferably, the steps of positioning the mean TSI path comprise steps of determining at least one final position in which the last data point of the TSI path is to be positioned, preferably such that this position is located in the myocardium. If these both steps are fulfilled, a set of possible positions of beginning and ending both fulfilling the said requirement will lead to a subset thereof in which all certain requirements of the next preferred embodiment is fulfilled.

As such, a further preferred embodiment provides that the steps of positioning the mean TSI path comprise steps of determining that the mean TSI path is fully located within the heart, preferably of a blood cavity of the heart and/or the wall thereof, such as the ventricles or the chambers.

It is most preferred that the positioning of the mean TSI path in the model of the heart fulfills these 3 preferred requirements. Based on fulfilling these 3 requirements, a very small set of possible solutions will be obtained, after which the method preferably determines the preferred solution of the set of possible solution is to be graphically rendered for display.

According to a further preferred embodiment, the method comprises steps of determining which of the TSI data values represents the last data point of the TSI path. As the end of an electrophysiological phase representing the ECG feature of interest is not a priori known, such endpoints needs to be determined in order to be able to both fit the $1^{st}$ and last point of the mean TSI path in the myocardium.

To this end, the method further preferably comprises steps to make a determination that a change of direction of the TSI path in the ending phase of the electrophysiological phase representing the ECG feature of interest represents the end of the electrophysiological phase. It is presently believed that for examples at the end of the QRS phase, when most of the myocardium has been depolarized, leading to providing a direction to the mean TSI path, the repolarization of the bulk of the myocardium that follows on the depolarization, provides a change of direction in the mean TSI path, shown as a final curve thereof. This happens e.g. somewhere between 80 and 180 ms after the onset of the QRS, preferably between 90 and 150 ms, more preferably between hundred and 40 ms. This mean TSI path curve is represented in the drawings relating to described embodiments below.

According to a further preferred embodiment the mean TSI value provides a position to be rendered within the boundaries of the heart representing a point per ECG measurement, such as per millisecond, and in which over the measurement of the ECG feature, such as the QRS, the combined points represent a line indicating the progress of the average position of successive isochrones of the development of the ECG feature, such as the activation front in case of a QRS. As such, the mean TSI path may be determined and plotted based on distinct measurements from the ECG recorder for example with an interval of a millisecond.

Further preferably, a propagation velocity of the ECG feature is a factor in calculating the mean TSI value.

Further preferably, the mean TSI is related to the vector cardiogram data.

Further preferably, a mean TSI is computed at successive predetermined time points during a cycle of the heart, such as per value in a range of 0.1 ms-5 ms, preferably 0.5 ms-3 ms further preferably 0.5 ms-2 ms, further preferably about 1 ms.

further preferably, the mean TSI is calculated while applying following formula:

$$\text{mean TSI}(x,y,z:t+1) = \text{mean TSI}(x,y,z:t) + v \cdot \text{VCG}(x,y,z:t)$$

in which t represents a time point of a number of time points, such as per millisecond, VCG represents a VCG data point of the ECG data, v is velocity of the ECG feature or the electrophysiological phase activity.

Further preferably, the method comprises steps of determining one or more areas of probability in which a first data value of the TSI path is located.

This preferred embodiment provides advantageously that for instance a location ventricular arrhythmia (VA) may be determined by correct positioning of the mean TSI path. The mean TSI path, when correctly placed in the heart model directly pinpoints the ventricular arrhythmia, such as a PVC when the initial point is location of the onset of the QRS, such as the activation thereof.

Further preferably, the method comprises steps of comparing the angle of the ECG feature axis, such as the QRS axis, with the TSI direction at or close to the respective area of probability, preferably comprising the steps of determining the area of probability of choice for positioning the beginning of the TSI path. If an above-described valid positioning of the mean TSI path, which is fully in the heart, beginning and ending in the myocardium, provides a direction of the mean TSI path that is closest to the direction of a QRS axis, then this is the most likely position of the mean TSI path in the heart, and therefore the most likely position of the ventricular arrhythmia is in the area of the beginning of the mean TSI path.

In order to provide a further graphical representation, such as in FIG. 2, according to a further preferred embodiment the VCG data is preferably subsequently added to the progressing mean TSI position. A preferred effect of such a way of correcting the VCG signal with the estimated mean TSI signal is that small signals are shown as a relative large change in signal. The initial ECG (first 40 ms) of a PVC is very low in amplitude, but actually does indicate a direction, difficult to be detected by signals analysis. This low amplitude signal gets amplified in a physiological way because it represents the progressing of initial activation through the myocardium.

A further aspect according to the present invention relates to a system for under application of a method according to one or more of the preceding claims provide a mean temporal spatial isochrone (TSI) path relating to an ECG feature (wave form) of interest, such as the activation of the heart from a single point (QRS), relative to the heart in a torso while using an ECG measurement from an ECG recording device, comprising:

a processing unit, a memory coupled with the processing unit, receiving means for receiving location information relating to a number of ECG electrodes, receiving means for receiving electro data of the respective ECG electrodes, outputting means for outputting of result data and/or results comprising image data. Such a system provides advantages such as described in relation to the above described aspect of the method.

According to a further preferred embodiment, the system comprises a recording device, such as an optical recording device for determining of a position of respective ECG electrodes relative to a torso.

Further preferably, the system comprises a display screen and inputting means for inputting of instructions.

For the purpose of providing a user-friendly system, the processing unit, the memory and the recording device are integrated in one physical housing, comprising in memory program coding means for performing of the method according to the present invention and preferred embodiments as indicated in the above.

BRIEF DESCRIPTION OF THE DRAWINGS

Further advantages, features and details of the present invention will be described in the following in greater detail relating to one or preferred embodiments in the reference to the drawings. Similar yet not necessarily identical parts of different preferred embodiments may be indicated with the same reference numerals.

DESCRIPTION OF THE INVENTION

Figure 1:
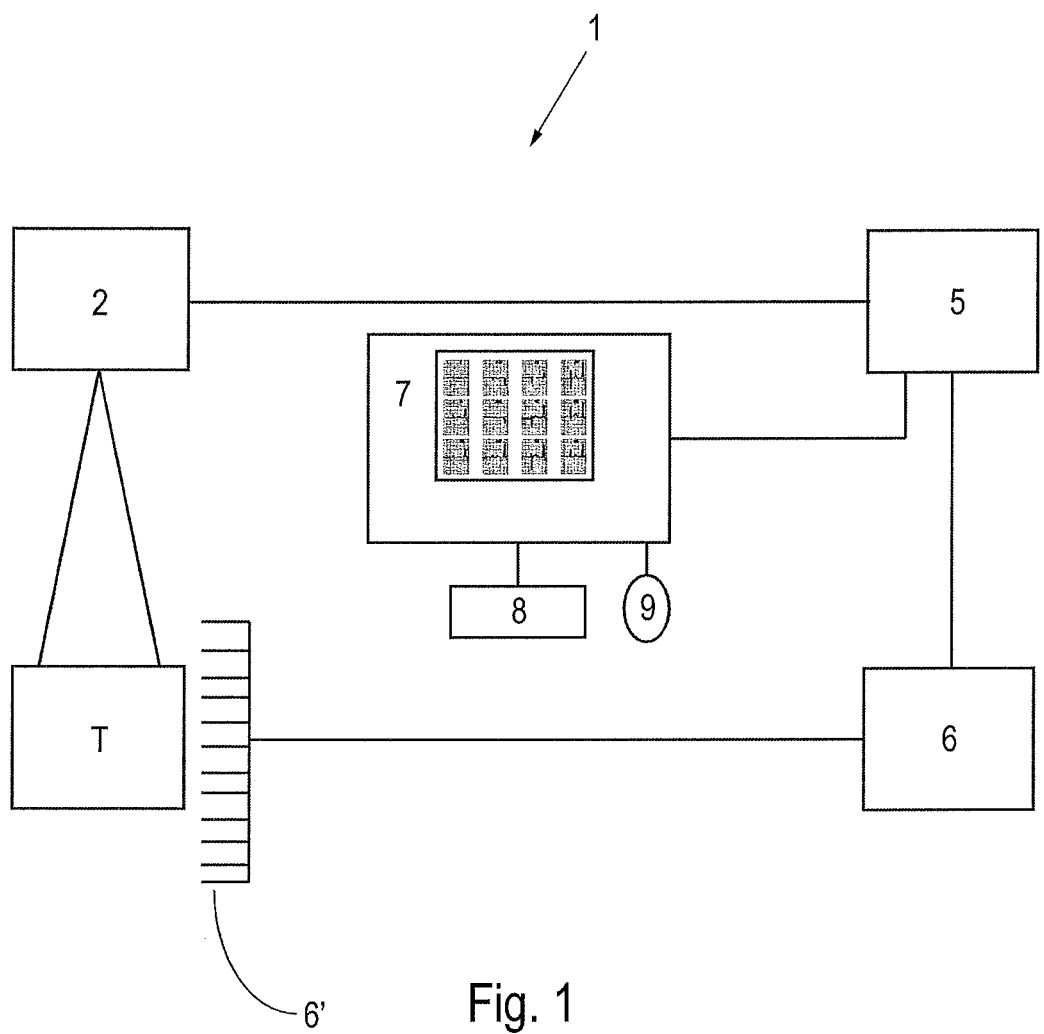
FIG. 1 is a block diagram of a preferred embodiment of a system according to the present invention.

A system according to the present invention, such as shown in FIG. 1, a preferred embodiment is shown of a system 1 for performing the method. A three-dimensional camera 2, for detecting ECG electrodes arranged at a torso T, is arranged above the torso T (schematically shown) of a person. The camera is suitable for moving thereof relative to the torso such that from several sides the torso can be recorded for detecting of the ECG electrodes in place. Data from the camera are transferred to a computer 5. The computer is connected to a monitor 7, keyboard 8 and mouse 9 for receiving input data from these peripherals from a user and for outputting of image data to the user. The computer is furthermore coupled with an ECG amplifier 6 that in its turn is coupled to ECG electrodes 3 on the torso T. A practical number of electrodes that is supplied is between 4 and 16, preferably substantially 12. A larger number for achieving a higher resolution is envisaged and use thereof dependent on the surroundings in which the installation is applied also usable. The skilled person would be able to determine the number of electrodes as a correct choice based on available equipment.

For example, for a P-wave or QRS complex, a VCG represents the activation direction at a certain time relative to an arbitrary reference point. This reference point represents the mean temporal-Spatial Isochrone (TSI) 12. Consequently the position of the mean TSI progresses within the heart space, approximately the myocardium and the blood cavities. As a result of this, the traditional VCG loop 11 can become a vector path or trajectory.

This invention describes a method to derive e.g. the mean TSI from the ECG, taking the mean TSI into account to correct for the VCG direction, relating the mean TSI and VCG to a standard heart geometry, or an estimated heart geometry or a patient specific heart geometry derived from medical images (MRI or CT).

Figure 2:
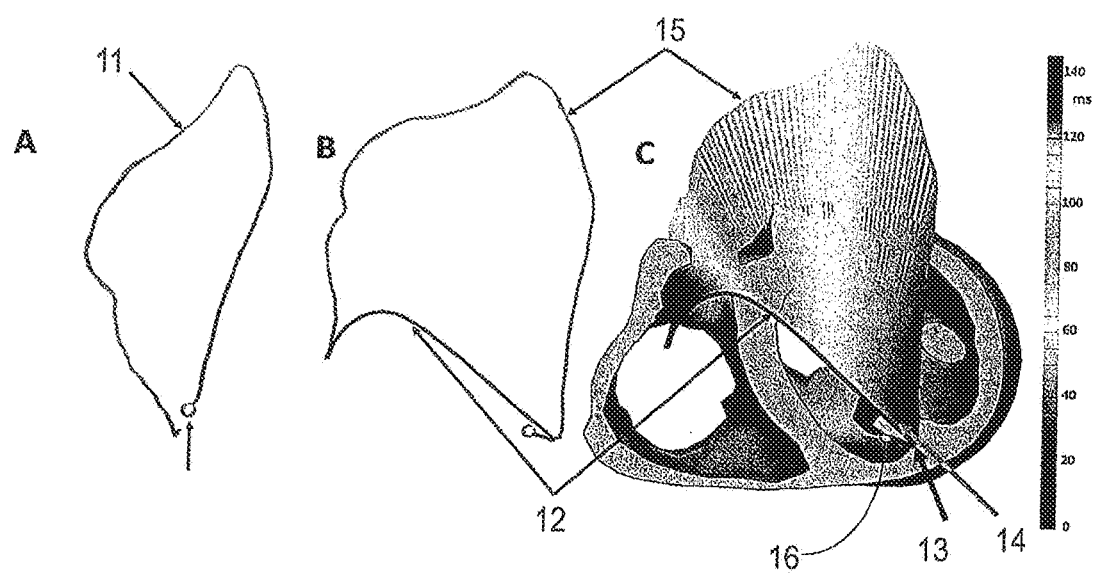
FIG. 2 is a graphical representation of path information and vector information in relation to a heart.

The invention is explained using the activation of the heart 15 from a single, point, FIG. 2, or a premature ventricular contraction (PVC). The invention is preferably also be applied to the P wave of the ECG.

The VCG signal gives the mean direction of activation. Assuming an propagating activation in case of the PVC, the position progresses in this direction. Assuming a default propagation velocity in the heart of $$v = 0.8 \frac{m}{s}$$

the position over time (position(t)) will be:

mean TSI(x,y,z:t+1)=mean TSI(x,y,z:t)+v·VCG(x,y,z:t)

for every ms (ECG sample).

The VCG signal is subsequently added to the progressing mean TSI position (see FIGS. 2b and 2c).

An effect of this way of correcting the VCG signal with the estimated mean TSI signal is that small signals are shown as a relative large change in signal. The initial ECG 13-14 (first 40 ms) of a PVC is very low in amplitude, but already shows a direction, difficult to be detected by signals analysis. This low amplitude signal is amplified in a physiological way because it represents the progressing of initial activation through the myocardium.

Figure 3:
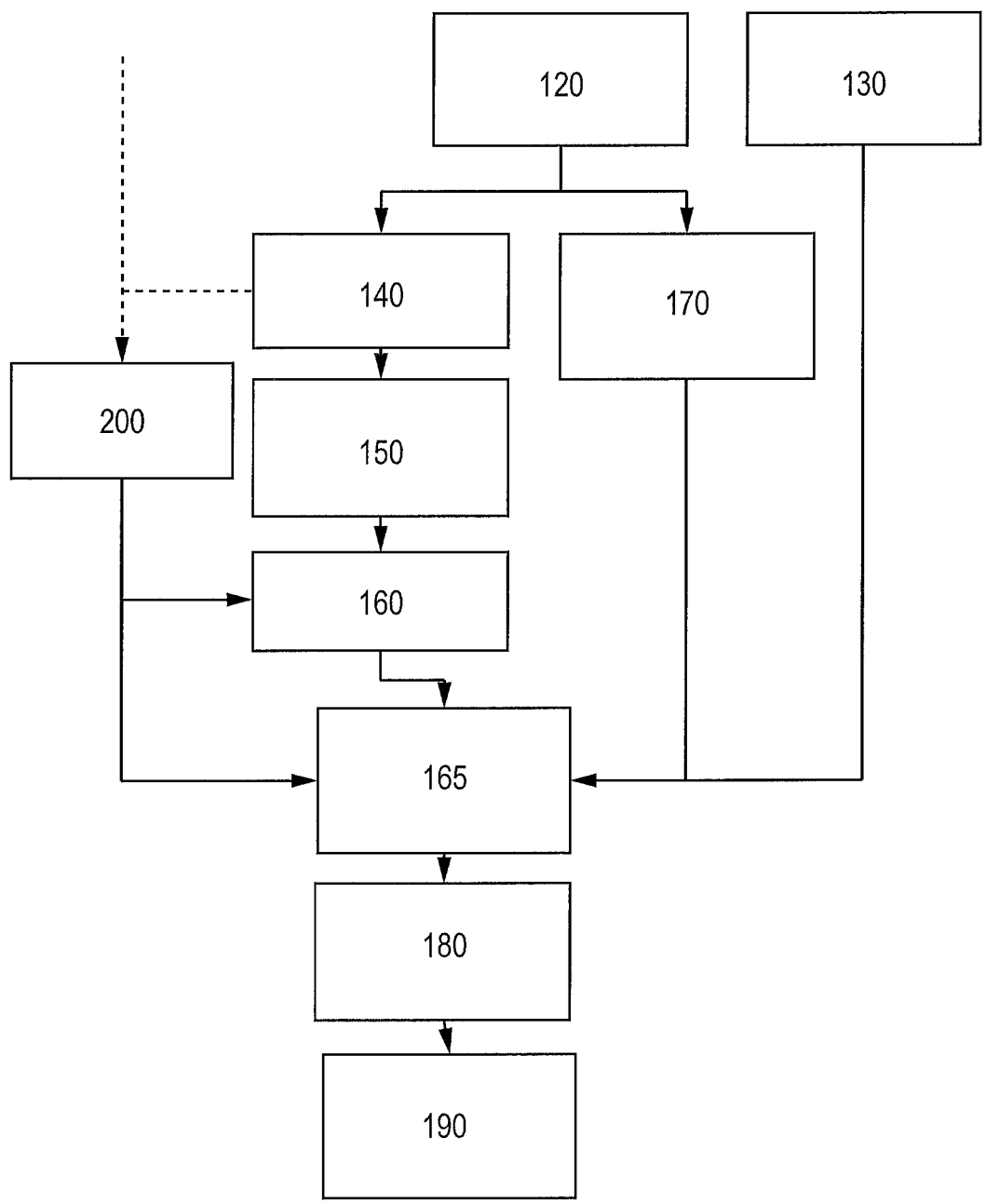
FIG. 3 is a flow diagram of a preferred embodiment according to the present invention.

Steps according to FIG. 3 comprise the following. In step 200, patient information is obtained and based thereon, a heart torso model based on available patient data is selected. Step 120 comprises recording an ECG, preferably by applying a standard 12 lead ECG. Step 130 comprises recording of the VCG directly, for instance using the frank lead system VCG, for which an ECG is required. The measuring of the ECG (120) and measuring of the VCG (130) is performed with ECG recording equipment. This can be ECG, e.g., standard 12 lead, that is known per se or any Body surface map system with any number of ECG leads.

Step 140 comprises taking a 3D image of the respective thorax with ECG electrodes applied on the chest. The result is a 3D recording indicating the positions of the ECG electrodes on the chest for using in selecting a heart torso model. In step 140 a 3D image is recorded with the 3D camera to localize the ECG electrodes relative to the thorax. The objective is to localize the 3D position of the ECG electrodes on the thorax. So both a hull of a part of the thorax is obtained as well as the electrodes on them. The camera enables the measurement of electrode positions for every individual ECG measurement. Both a single movable camera and a plurality of stationary cameras are envisaged to cover the relevant surface parts of the thorax for a sufficient 3D recording.

In step 150, the location of the ECG electrodes is determined in the 3D recording and model. In step 160 the information relating to the ECG, electrodes and the selected heart torso model is converted into a VCG representation.

In step 170, a standard matrix ECG to VCG conversion is performed. In step 180, the mean TSI is computed and the position of the origin of the vector signals is corrected. In step 190, an orthogonal view of the respective cardiac anatomy is created and the signals are projected in the three views of the heart and the results are displayed in these views.

Three ways to obtain an vector signal are described. The first preferred method comprises measuring of an ECG (120) and converting it patient specifically by means of steps as 140 and 150 to a VCG signal. Such method takes aspects of the anatomy into account, such as a) the body build, b) heart shape and position, and c) the electrode position. As such, this the preferred route, because patient specific data are used in performing the determinations.

A second method comprises steps of Measuring an ECG (120) and converting the same using a transformation matrix (170) into a VCG signal. Applying such transformation matrices comprises the use of a statistical approach. Such transformation matrix approach converts the standard 12 lead ECG into three x,y,z signals of the VCG. The matrix coefficients preferably represent an average patient conversion, i.e. the mean body build lead locations etc.

A third method comprises measuring of an VCG directly (130). The VCG can be measured directly using a specific lead system, e.g. the frank lead system, or a body surface map from which a Gabor-Nelson VCG can be constructed. The frank lead system has been designed using a homogeneous volume conductor model. This model is used to compute the x,y,z signals of the VCG from the measured ECG signals at predefined electrode positions. The Gabor-Nelson integrates the potentials on the body surface.

In step 150, the electrodes need to be detected from the 3D photographic image in the 3D space. Automatic detection is preferably performed based on visible features of the electrode as present on the thorax, such as the color of the electrode or the shape of the electrode.

In step 160, the objective is to compute the x, y, z signals of the VCG as a weighted sum of the ECG signals and a normalized vector between the heart and the ECG electrode, for which reference is made to WO 2017/099582 incorporated herein with reference. The weight ($\alpha_n$) per ECG signal is preferably set equal or is preferably derived from a volume conductor matrix, representing the contribution of the heart surface potentials to the potentials measured at the ECG electrode location.

In step 200, a torso model or heart torso model is retrieved from the patient either from a database or from MRI or other 3D imaging methods or systems. The objective is to determine and/or estimate a relationship between the heart and said ECG electrodes. The more patient specific the torso model and or the heart torso model is, the more accurate this relation can be determined.

$$VCG = \sum_{n=1}^{leads} \alpha_n \cdot \frac{(p_{heart} - p_{ECG\,electrode})}{\|p_{heart} - p_{ECG\,electrode}\|} \cdot ECG_n$$

An advantage of this VCG computation system is that the electrode position, heart position and/or orientation of the heart is the basis of this relationship. The value of $\alpha_n$ can be derived from the standard deviation of the row of the volume conductor transfer matrix or it can be dependent on the time of the measurement, such as when using the depolarization direction derived from the mean QRS axis.

In step 165, the mean QRS axis is computed, which represents the major direction of activation. For PVC's and VT's the major mean QRS direction originates from the region from where the PVC/VT originates. A summation of the VCG signal from 160 over time results in the mean QRS axis direction, which is preferably positioned at the center of mass of the viable ventricular myocardium.

$$\text{mean } QRS \text{ vector} = \int_{t=QRS\,onset}^{QRS\,end} VCG(t)\,dt$$

Figure 4:
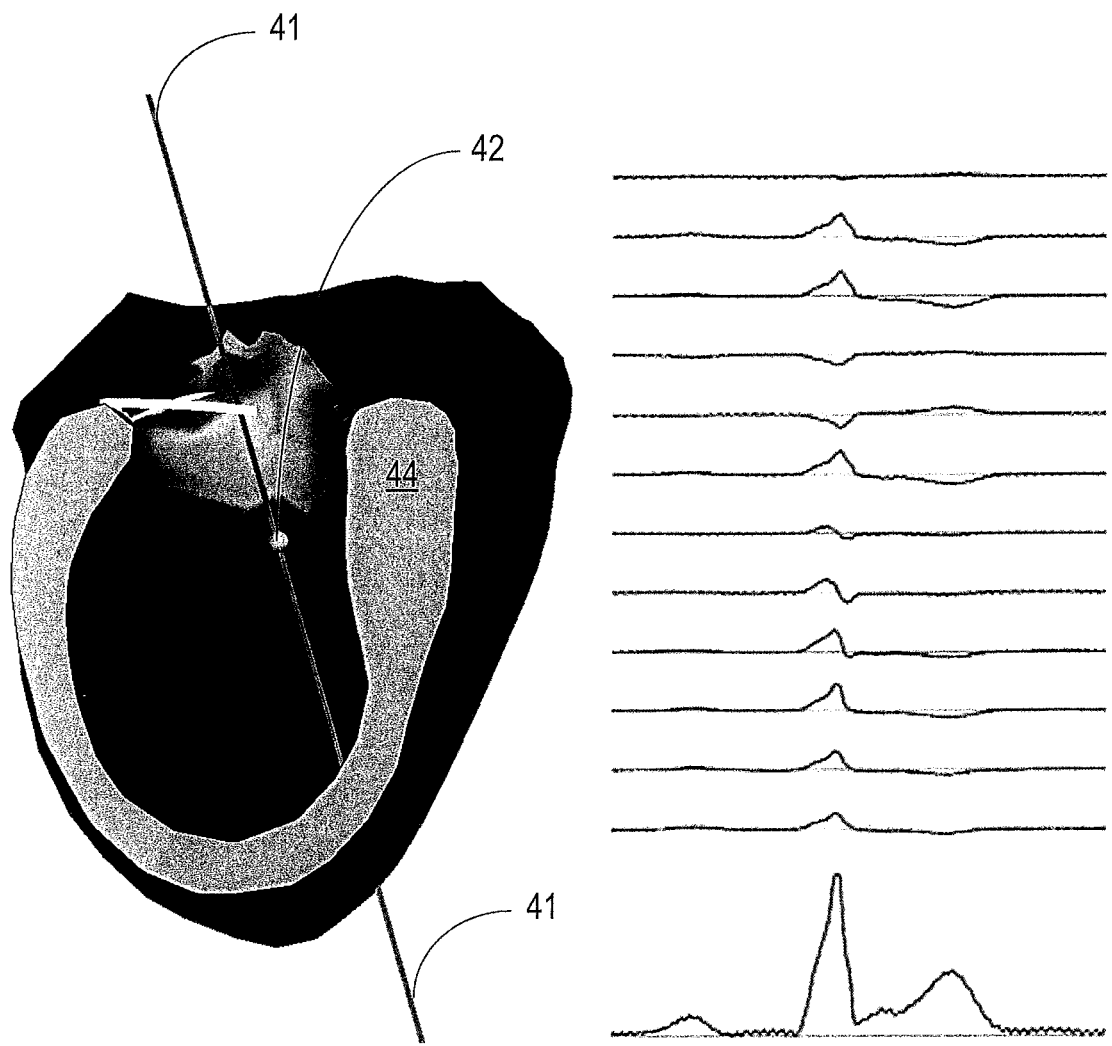
FIG. 4 is a graphical representation of a mean QRS axis of the ECG in a heart.
Figure 5:
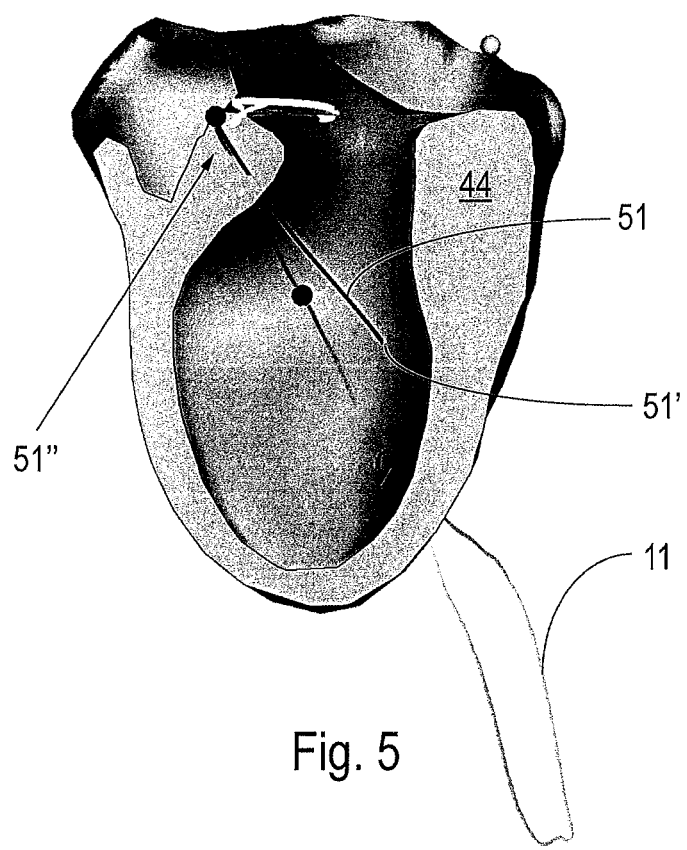
FIG. 5 is a graphical representation of path information and vector information relation to a heart.
Figure 6:
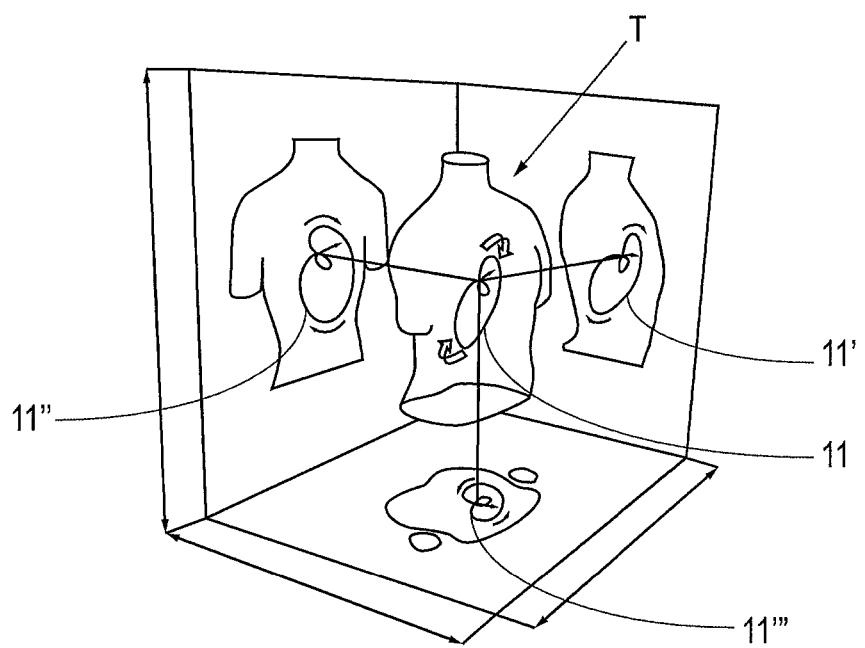
FIG. 6 is a torso plane representation of a preferred embodiment according to the present invention.
Figure 7:
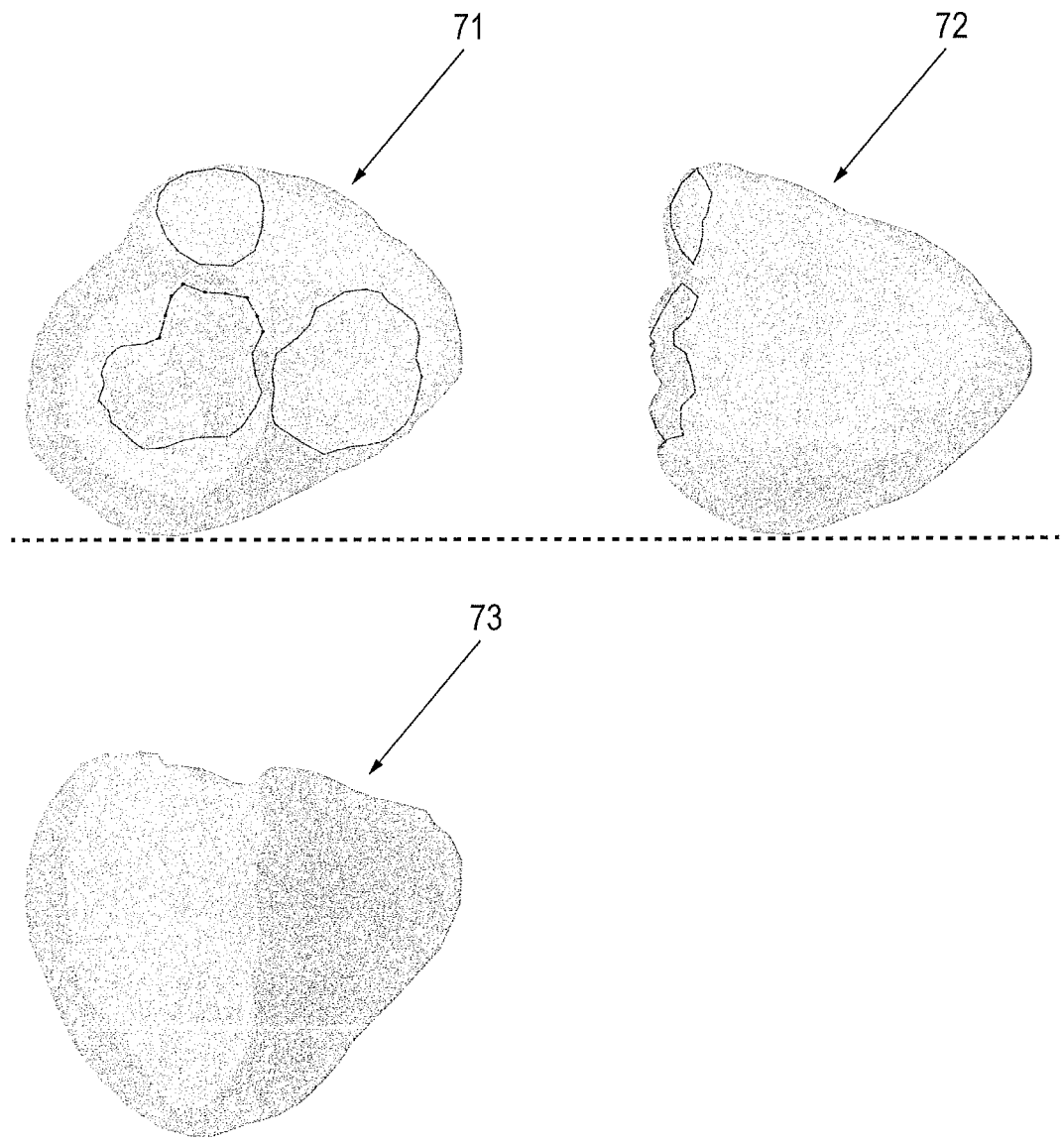
FIG. 7 is a projection representation of a preferred embodiment according to the present invention.
Figure 8:
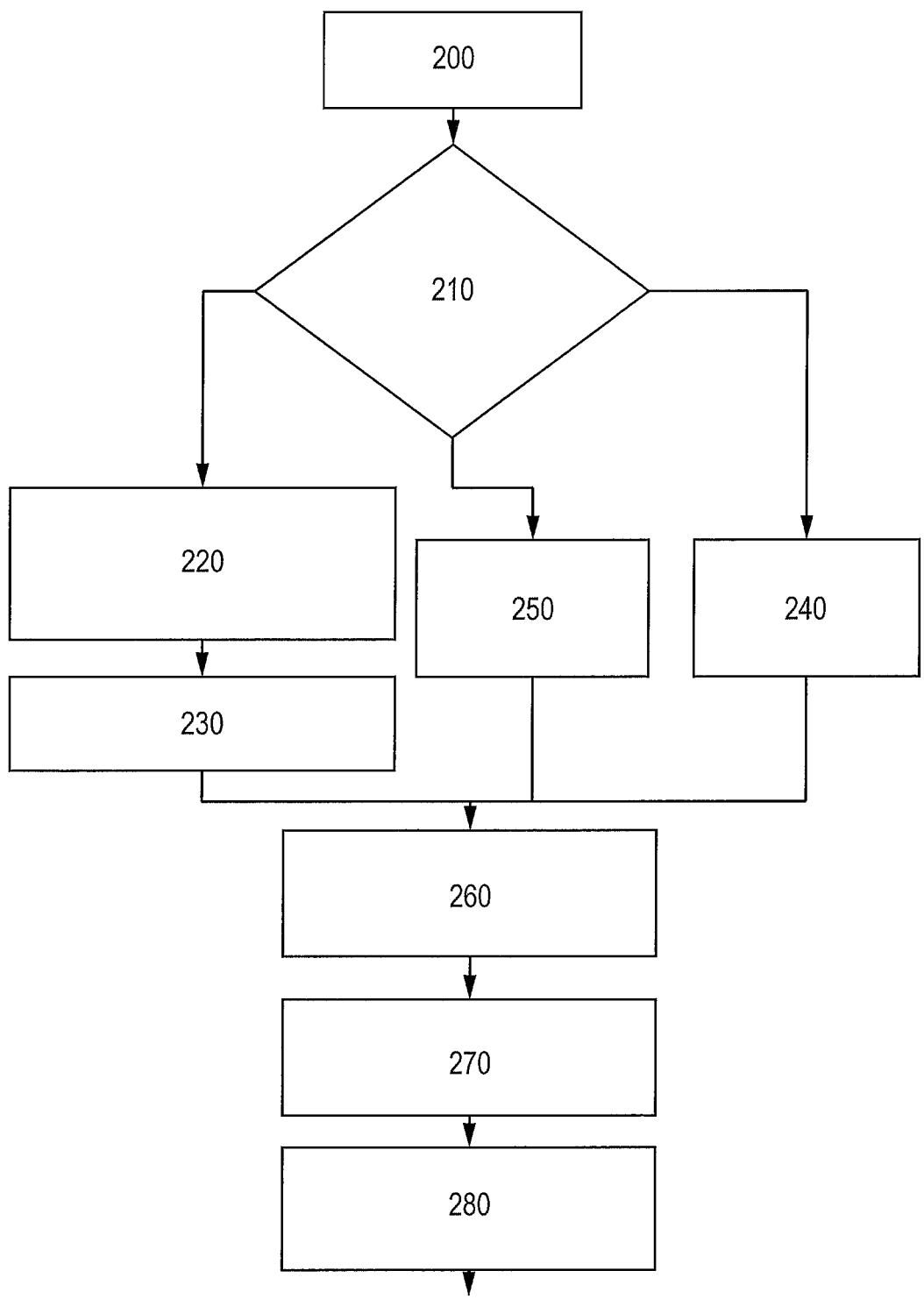
FIG. 8 is a flow diagram of a preferred embodiment according to the present invention.

The mean QRS axis of the ECG is shown in FIG. 4 with reference numeral 41. The center of the ventricular mass is shown with reference numeral 42. The center of mass is used to take into account the shape of the ventricular anatomy. Hypertrophic parts of the heart (thicker wall) are thus for example accounted for, some for dilated hearts.

In step 180, the VCG indicates the direction in which the activation is progressing at each time of the ECG, it however does not provide an indication as to where the activation is located. The mean TSI (temporal spatial isochrone) is an estimation of a, preferably spatial, position of an isochrone in the myocardium at a certain point in time (temporal) of the ECG.

Where the VCG represents the direction of activation and as such provides a limited indication as to the cardiac anatomy, the mean TSI represents the mean activation wave front and consequently preferably is located within the heart, either the blood cavity or the myocardium. This position thus provides an indication from which region the electrical ECG signal is originating. For an activation from LVOT, the mean TSI 51 starts at the origin 51" of activation of the heart and ends in the area 51' activated last. The mean TSI can be computed in several ways.

Firstly, the VCG provides an indication of the direction of activation and consequently of the direction of progress of the mean TSI. Assuming a uniform propagation velocity, the mean TSI is preferably displaced every ms in the direction of the VCG with that constant speed.

Secondly, the simulated activation sequence for an activation sequence in an area close to the mean QRS axis is applied as a basis to compute the mean TSI for every time instant.

A major advantage of the mean TSI is that it provides an indication of the latest activated region of the heart, as it progresses into the region activated last.

For instance, in a patient with a left bundle branch block (LBBB) the activation starts on the right and ends in the left. In such instance, the mean TSI progresses from an area activated first at the right side of the heart to the area activated last on the left side of the heart. Once the mean TSI has been established the VCG signal is recomputed using the progressing position of the vector representing the VCG signal.

In step 190 The visualization of the VCG and mean TSI can be represented in color as shown in FIG. 2 in grey shades which enables a physician to interpret, in a user friendly manner, the visual relation between direction, position and the cardiac anatomy.

The more the model of the heart corresponds with the anatomy of the patient, the stricter the rules on the mean TSI and VCG construction can be maintained. For a patient specific heart model the mean TSI preferably remains inside the myocardial heart space. This provides support to obtain a respectively accurate reconstruction of mean TSI and VCG.

With the above description the first mean TSI position is not determined. Without availability of a respective cardiac anatomy, an arbitrary reference point is preferably used. A relation to the cardiac anatomy provides support relating to a diagnosis. Traditionally the VCG signal is shown in the orthogonal planes of the torso.

The representations of the mean TSI and VCG signal have a direct relation with the cardiac anatomy from which the ECG signals are originating. Further preferably, the heart orientation is used as a basis for projecting the signals on the cardiac anatomy. A LAO (from base to apex), ROA (from right to left chamber), and the 4-chamber projection view (anterior to posterior) are preferably used.

The cardiac anatomy is preferably obtained from an MRI scan or CT scan performed on the patient, selected from a model database, or a general model is used. In case more than one model is available, such as models that are not directly based on the anatomy of the respective person, the selection of the best fitting model is preferably, at least in part, based patient data, like age, height, chest circumference, further preferably estimated from a 3D photo, or from an echo image. To project the torso oriented VCG onto the heart oriented VCG, the long axis and the left-right axis need to be known. The long axis is determined by the line between the point representing the mean of the aorta and/or mitral valve and the apex of the left chamber. The left-right axis is perpendicular to the long axis and is determined by the line between the point representing the mean of the mitral valve and the mean of the tricuspid valve. These axes are preferably determined from the MRI or CT images or optionally determined by means of indicative manual input by means of e.g. the keyboard and/or mouse. In case no patient specific heart model is available the respective long and left-right axis is preferably estimated from general descriptions of the patient or the 3D image, such as the weight, height, chest circumference, etc. However, although decreases in exactness would affect embodiments according to the invention, such embodiments also function if such types of data are only partly.

In step 200, a hear model or heart torso model of the patient is obtained or selected from a plurality of obtainable models. When imaging data, such a obtained by means of MRI or CT imaging, is available a patient specific model can be created (240). This is the most accurate method, but always requires the imaging, which for a standard 12 lead ECG only is not be available. For those situations, an estimation of the patient model can be created based on known characteristics of the patient in steps 220, optionally with step 230. If also such patient characteristics are unavailable, a general model can be used in step 250. This later situation is for instance applicable when only an ECG is available and the ECG is converted into a VCG through a matrix transform, such as in step 170.

In step 210, it is determined what info is available to select the model, such as patient specific information, with or without 3D imaging, general information, or model information from a model database.

In step 240, a patient specific model of the heart and torso is assembled based on such imaging data, such as disclosed in WO 2017/099582. Optionally, in step 250, use is made of a general model. This model uses a standard model of the heart and torso and thus also 12 lead ECG electrode positions.

In step 220, the most appropriate model from the model database is selected. The model database preferably contains several models of different patient types, such as a) a normal heart for different age groups; or b) genetically influenced morphological hearts. An example thereof is ARVC patients, for which the right base is generally somewhat lower and they often have an enlarged right chamber. A further example comprises tetralogy of Fallot patients, which have very specific cardiac anatomy changing over time. A still further example comprises patients with hypertrophic heart diseases. Within such scope, many other types of hearts are envisaged to be included in such data base.

Several selection criteria can be used to select the right model are Age, Height, Weight, Chest circumference, Thorax height and/or Genetical profile.

Preferably a 3D photo is available from which the chest circumference and/or the length of the thorax can be obtained. This chest circumference and height is preferably used in selecting the right model. For genetically diseased patients the information is preferably added separately.

In step 230, the heart orientation of the selected model is corrected for the heart orientation of the patient as observed or derived based on patient parameters as indicated in the above. An example thereof is that the chest circumference, as is preferably derived from the 3D photo, has a relation with the heart orientation. A larger chest circumference indicates for instance that the patient has a bigger belly area, thus pushing the heart in a more horizontal position.

The orientation of the heart is preferably expressed by two rotations. A first rotation is a rotation to align the long axis of the heart with the estimated long axis direction. A second rotation is a rotation over the long axis such that the axis between mitral valve and tricuspid valve aligns with the estimated direction.

In step 260 the corrected long axis of the heart is determined to enable a LAO projection view of the heart. This way the VCG can be visualized in this plane which relates the VCG and mean TSI directly to the cardiac anatomy. Such feature provides a diagnostic value of the ECG/VCG/mean TSI has such graphical representation is readily interpretable.

In step 270, the corrected axis between mitral valve (LV) and tricuspid valve (RV) is determined to enable a RAO projection view of the heart. This LV-RV axis is preferably orthogonal to the long axis of the heart. This way the VCG is preferably visualized in this plane which relates the VCG and mean TSI directly to the cardiac anatomy. Such feature provides a diagnostic value of the ECG/VCG/mean TSI in step 280, based on the two axes, a third axis is defined as the one orthogonal to these two orthogonal axes. Each of the axis are preferably used to create a 2D projection of the heart, such as the LAO, ROA, and/or four chamber view.

Figure 9:
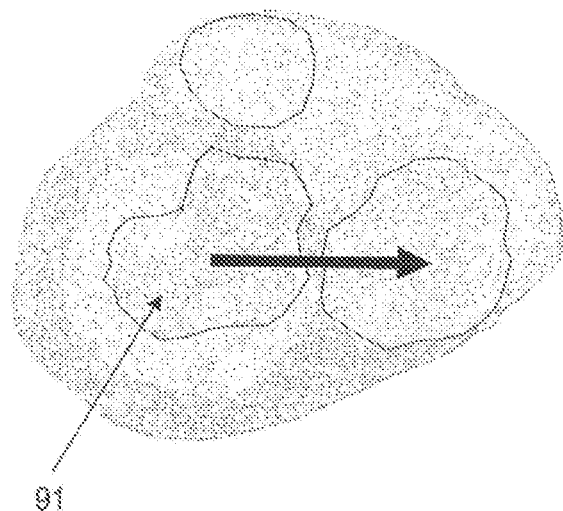
FIG. 9 is a projection representation of a preferred embodiment according to the present invention.
Figure 9:
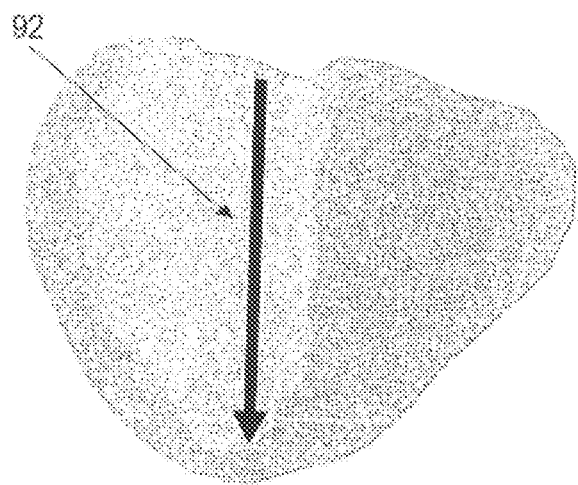
Figure 10:
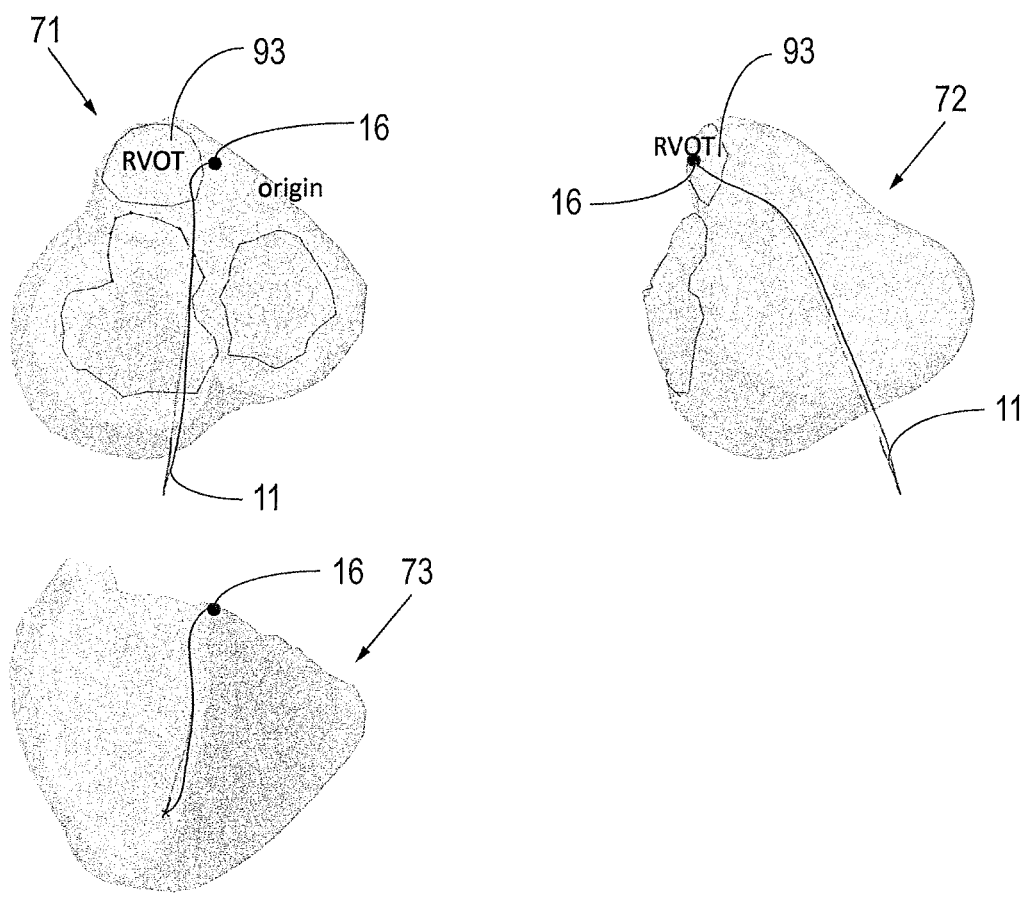
FIG. 10 is a projection representation of a preferred embodiment according to the present invention.
Figure 11:
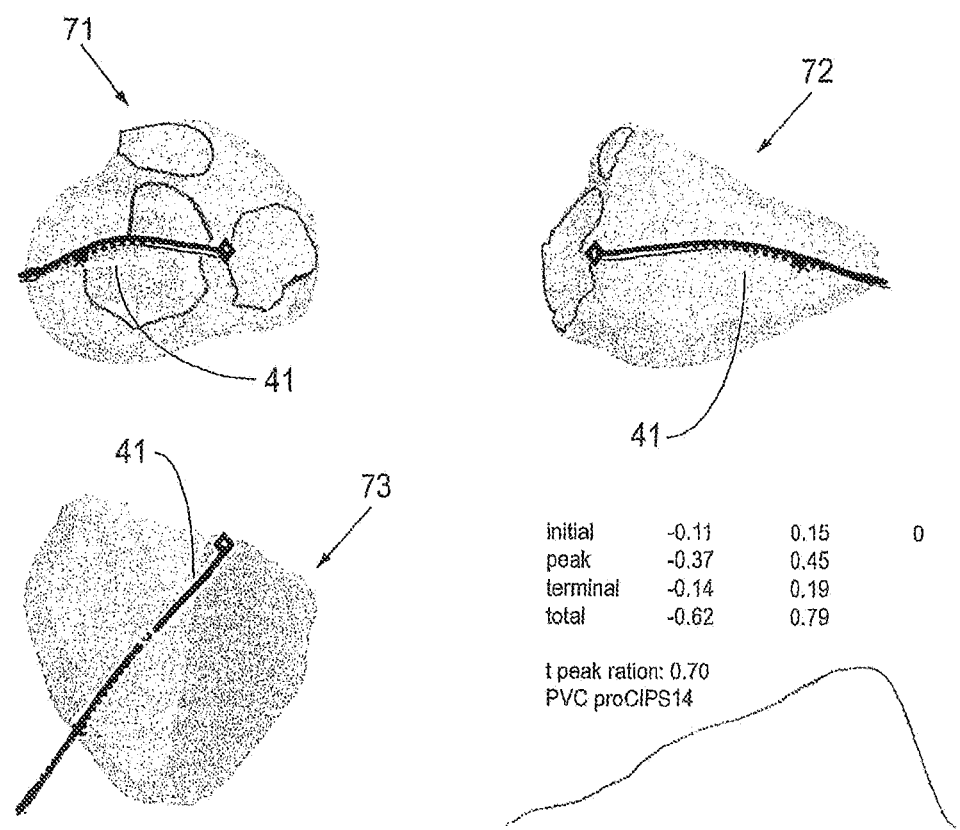
FIG. 11 is a projection representation of a preferred embodiment according to the present invention.
Figure 12:
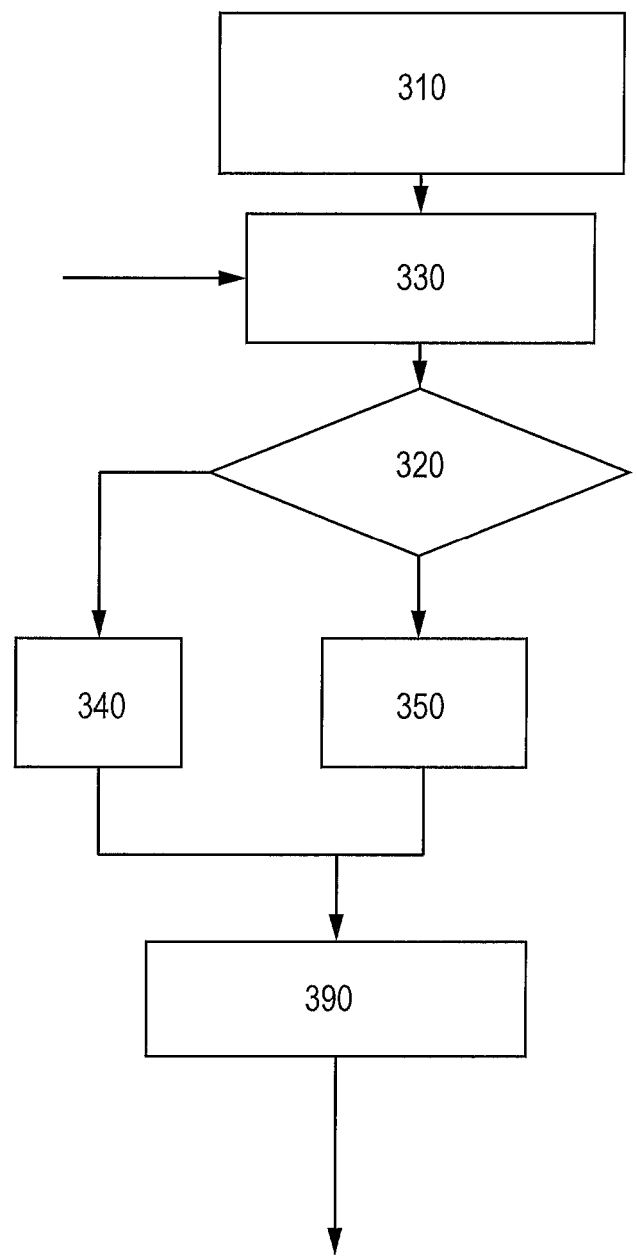
FIG. 12 is a flow diagram of a preferred embodiment according to the present invention.
Figure 13:
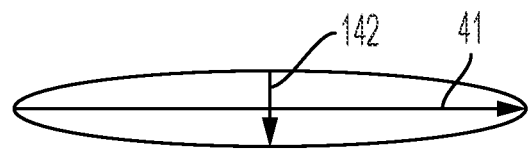
FIG. 13 is a graphical representation of a preferred embodiment according to the present invention.
Figure 14:
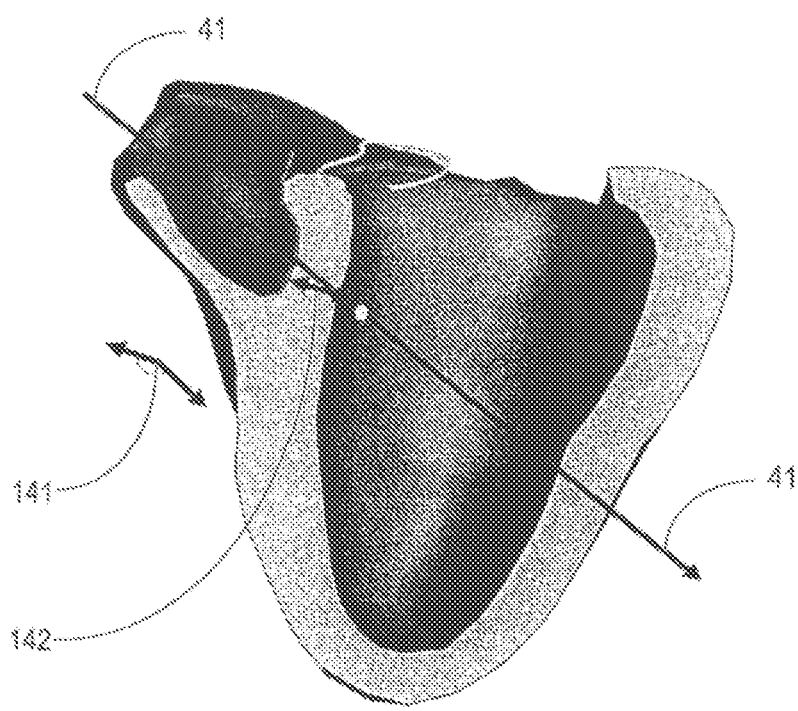
FIG. 14 is a graphical representation of vector information in relation to a heart.

In FIGS. 9-11, an example of the VCG from PVC (single focus activation) signal as computed with the embodiment described projected on the 3 heart planes 71, 72, and 73. It can be readily observed that the PVC originates from the RVOR region 91 and progresses 92 from the RVOT 93 to the left apical posterior wall.

The center of mass 11, i.e. either ventricles or atria, is preferably used as the reference point for the mean TSI and VCG signals. Further preferably, the position of the VCG and mean TSI signals is shifted over the cardiac anatomy to match the heart space, i.e. the mean TSI preferably remains inside the atrial or ventricular heart space. The ventricular heart space is used for ECG phenomena originating from the ventricular electrical activity, the atrial space for activity originating from the atria.

For ectopic activations, the center of mass is not the most appropriate place to let the mean TSI and consequently the VCG start as it starts from one point. To determine the origin of the PVC the mean QRS axis 41 is determined, for instance by taking the integral of the VCG signal directly derived from the ECG, as in step 140 or by measurement, as in step 130, according to the following formula.

$$\text{mean } QRS \text{ axis} = \int_{t=QRS\,begin}^{QRS\,end} VCG(x, y, z; t)\,dt$$

As the mean activation follows this mean QRS axis by approximation, the origin 16 is preferably close to a point along this mean QRS axis extending through the center of mass. For the largest part of the heart the origin of the PVC is found close to the point where the mean QRS axis leaves the ventricular heart space, i.e. leaves the ventricular myocardium or ventricular blood cavity (see FIG. 10).

For septal or papillary muscles an exception is preferably made. Further analysis of the VCG signal and mean TSI is required to localize it appropriately. To distinguish the ventricular septum from the right free wall the initial part of the VCG signal is analyzed. If the initial activity initially progresses in an opposite direction than the mean QRS axis the activity originates from the septum. For PVC's originating from papillary muscles the VCG signal shows a less uniform direction of activation as the activation follows a more complex path. This complexity can be used to localize the origin to the appropriate anatomical structure.

A similar procedure is preferably followed for atrial ectopic activity, such as by analyzing the P wave and using the atrial geometry. For Normal His-Purkinje activation the center of the ventricular mass is a good initial estimate, as well as for the T-wave.

For complex anatomical hearts an adapted center of mass is preferably applied, for instance in Tetralogy of Fallot patients.

In step 310, the ECG contains both the activation and recovery of the atria and ventricles. Each part is preferably approached differently for analysis. A selection regarding which feature of the ECG is going to be analyzed is made, such as P-wave or QRS complex.

In step 320, a computation of the center of mass of the atria and ventricle is performed. This point is preferably used as an anchor point for the VCG and mean TSI signals. For heavily deformed hearts the center mass is preferably adapted.

In steps 330, 340, 350 the mean axis per feature is determined. Here the example will be shown for the QRS, but it also applies for the P wave.

$$\text{mean QRSvector} = \int_{t=QRS\ onset}^{QRS\ end} VCG(t)dt$$

Where the mean QRS vector runs through the center of the heart mass.

In step 380, the deviation angle and distance of the VCG direction and the mean QRS is computed, preferably one value over the whole activation cycle, preferably related to the anatomy. The purpose is to be able to improve the classification of the ECG feature and to correct the origin of the VCG and mean TSI.

The distance is a measure of the variation in vector direction and can also be expressed as the first and second eigen value of the VCG, representing the first and second order axis in which the VCG is drawn.

For a PVC for instance originating from a single point, the dominant region will be in one direction, consequently the length of axis 142 will be much smaller than axis 41. This can also be expressed in the distance of the VCG to the mean axis line. The larger the mean of this deviation distance is, the larger the second axis. The advantage of using the deviation angle 141 or the deviation distance is that it enables the analysis of parts of the VCG or mean TSI. For instance, if the deviation angle of the initial part of the VCG/mean TSI has an opposite direction to the mean QRS axis this is indicative of about the distinction in endo versus epi direction, or the distinction between septal RVOT versus anterior RVOT.

The x,y,z signals of the VCG and mean TSI can be represented in color, i.e. every time sample the line will change color so it is easy to understand where the signals start and where they end.

A further aspect according to the present invention comprises a method to estimate a mean temporal spatial isochrone (TSI) path through the heart from a vector signal derived from the ECG or directly measured (vector cardiogram using the Frank lead system), electrode positions, and heart position, preferably in which a position of the vector changes every time sample in a direction indicated by the vector signal. Further preferably, vector position changes are limited to the heart space, such as that the VCG vector position remains within the epicardial boundaries (blood cavities or myocardium). It is preferred that the speed of vector position change per time sample is set as a variable over time or set at a fixed value.

Further preferably, the VCG direction and position is be visualized in an orthogonal heart system, LOA view (apex to base), ROA view, anterior to posterior, and the 4 chamber view (inferior to superior). Electrode and heart positions are preferably obtainable or obtained from a model database. Electrode positions are obtainable or obtained from a 3D imaging recording.

Further preferably, thorax dimensions, optionally derived for a 3D image, are used to select the most appropriate heart model. Such model selection is preferably adapted by the use of a further user input, such as genetical defects, weight, known morphological aberrations in the heart morphology, etc.

7) Vector signals (VCG) can be computed in the way described in the vector patent, but also by a transformation matrix such as the Dower transform. This matrix converts a 12 lead ECG into XYZ signals for the VCG.

8) The orthogonal heart system is obtained by determining the long axis of the heart (from MRI, model or echo) and the axis between the mid mitral valve and the mid tricuspid valve. The third axis is perpendicular to these two axis.

The present invention has been described in the foregoing on the basis of several preferred embodiments. Different aspects of different embodiments are deemed described in combination with each other, wherein all combinations which can be considered by a skilled person in the field as falling within the scope of the invention on the basis of reading of this document are included. These preferred embodiments are not limitative for the scope of protection of this document. The rights sought are defined in the appended claims.

The invention claimed is:

1. A method to provide a mean temporal spatial isochrone (TSD path relating to an electrocardiograph (ECG) feature (wave form) of interest relative to a heart in a torso while using an ECG measurement from an ECG recording device, the method comprising steps of:
   receiving ECG measuring data from the ECG recording device,
   determining vector cardiogram (VCG) data,
   receiving a heart model as an input,
   obtaining location information relating to a number of ECG electrodes relative to the heart model,
   based on the obtained location information relating to the number of ECG electrodes relative to the heart model, positioning of the number of ECG electrodes, determining mean TSI data values representing a mean TSI path relating to an electrophysiological phase representing the ECG feature, the mean TSI path providing a location within the heart representing a mean location of the ECG feature at the corresponding time,
   positioning the mean TSI path and the VCG data in the heart model at an initial position, and displaying on a display screen a rendering of the heart model with the mean TSI path and the VCG data.

2. The method according to claim 1, wherein the step of positioning the mean TSI path comprises using a predetermined position for positioning a first data value of the mean TSI path.

3. The method according to claim 1, wherein the step of positioning the mean TSI path comprises determining at least one initial position in which a first data point of the mean TSI path is to be positioned.

4. The method according to claim 2, wherein the step of positioning the mean TSI path comprises determining at least one final position in which a last data point of the mean TSI path is to be positioned.

5. The method according to claim 1, wherein the step of positioning the mean TSI path comprises determining that the mean TSI path is fully located within the heart.

6. The method according to claim 1, further comprising determining which of the mean TSI data values represents the last data point of the TSI path.

7. The method according to claim 6, further comprising making a determination that a change of direction of the mean TSI path in an ending phase of an electrophysiological phase representing the ECG feature of interest represents the end of the electrophysiological phase.

8. The method according to claim 1, wherein the mean TSI data values provide a position to be rendered within the boundaries of the heart representing a point per ECG measurement and in which over measurement of the ECG feature combined points represent a line indicating a progressing of an average position of successive isochrones of the ECG feature.

9. The method according to claim 1, wherein a propagation velocity of the ECG feature is a factor in calculating the mean TSI data values.

10. The method according to claim 1, wherein the mean TSI path is related to the VCG data.

11. The method according to claim 1, wherein the mean TSI path is computed at successive predetermined time points during a cycle of the heart.

12. The method according to claim 11, wherein the mean TSI path is calculated while applying following formula:

$$\text{mean TSI}(x,y,z:t+1) = \text{mean TSI}(x,y,z:t) + v \cdot \text{VCG}(x,y,z:t)$$

wherein:
t represents a time point of a number of time points,
VCG represents a VCG data point of ECG data, and
v is velocity of the ECG feature or activity of the electrophysiological phase.

13. The method according to claim 1, further comprising determining one or more areas of probability in which a first data value of the mean TSI path is located.

14. The method according to claim 13, further comprising comparing an angle of an ECG feature axis with a TSI direction at an area of probability.

15. The method according to claim 1, wherein the VCG data is subsequently added to a progressing mean TSI position.

16. A system for application of a method to provide a mean temporal spatial isochrone (TSI) path relating to an electrocardiograph (ECG) feature (wave form) of interest relative to a heart in a torso while using an ECG measurement from an ECG recording device, the method comprising steps of:
receiving ECG measuring data from the ECG recording device,
determining vector cardiogram (VCG) data,
receiving a heart model as an input,
obtaining location information relating to a number of ECG electrodes relative to the heart model,
based on the obtained location information relating to the number of ECG electrodes relative to the heart model, positioning of the number of ECG electrodes,
determining mean TSI data values representing a mean TSI path relating to a electrophysiological phase representing the ECG feature, the mean TSI path providing a location within the heart representing a mean location of the ECG feature at the corresponding time,
positioning the mean TSI path and the VCG data in the heart model at an initial position, and
displaying on a display screen a rendering of the heart model with the mean TSI path and the VCG data.
the system comprising:
a processing unit,
a memory coupled with the processing unit,
means for receiving location information relating to a number of ECG electrodes,
means for receiving electro data of the respective ECG electrodes, and
means for outputting of result data and/or results comprising image data.

17. The system according to claim 16, further comprising a recording device for determining a position of respective ECG electrodes relative to a person.

18. The system according to claim 16, further comprising a display screen and inputting means for inputting of instructions.

19. The system according to claim 16, wherein the processing unit, the memory and the recording device are integrated in one physical housing, comprising in memory program coding means for performing the method.

* * * * *

UNITED STATES PATENT AND TRADEMARK OFFICE
CERTIFICATE OF CORRECTION

PATENT NO. : 11,612,349 B2
APPLICATION NO. : 16/605286
DATED : March 28, 2023
INVENTOR(S) : Eelco Mattias van Dam et al.

It is certified that error appears in the above-identified patent and that said Letters Patent is hereby corrected as shown below:

In the Claims

Column 12, Line 38, Claim 1, delete "(TSD" and insert -- (TSI) --

Signed and Sealed this
Twenty-third Day of May, 2023

Katherine Kelly Vidal
*Director of the United States Patent and Trademark Office*